United States Patent
Amaki et al.

(10) Patent No.: US 9,504,257 B2
(45) Date of Patent: Nov. 29, 2016

(54) **STRAIN BELONGING TO *BACILLUS* GENUS, MICROBIOLOGICAL AGENT, AND PLANT CULTIVATION METHOD**

(75) Inventors: Yusuke Amaki, Ibaraki (JP); Keijitsu Tanaka, Ibaraki (JP); Motoki Tanaka, Ibaraki (JP); Akitomo Takahashi, Tokyo (JP)

(73) Assignee: SDS BIOTEK K.K., Tokyo (JP)

( * ) Notice: Subject to any disclaimer, the term of this patent is extended or adjusted under 35 U.S.C. 154(b) by 122 days.

(21) Appl. No.: 14/119,022

(22) PCT Filed: May 21, 2012

(86) PCT No.: PCT/JP2012/062935
§ 371 (c)(1),
(2), (4) Date: Feb. 27, 2014

(87) PCT Pub. No.: WO2012/161160
PCT Pub. Date: Nov. 29, 2012

(65) Prior Publication Data
US 2014/0179528 A1 Jun. 26, 2014

(30) Foreign Application Priority Data
May 26, 2011 (WO) .................. PCT/JP2011/062109

(51) Int. Cl.
*A01N 63/00* (2006.01)
*C12N 1/20* (2006.01)
*A01N 63/02* (2006.01)
*C12R 1/07* (2006.01)

(52) U.S. Cl.
CPC .............. *A01N 63/02* (2013.01); *A01N 63/00* (2013.01); *C12N 1/20* (2013.01); *C12R 1/07* (2013.01)

(58) Field of Classification Search
None
See application file for complete search history.

(56) References Cited

U.S. PATENT DOCUMENTS 6,524,998 B1 * 2/2003 Kloepper ............... A01N 63/00
504/100

FOREIGN PATENT DOCUMENTS

| JP | 2955655 | B2 | 10/1999 |
|---|---|---|---|
| JP | 3471811 | B2 | 12/2003 |
| JP | 3471815 | B2 | 12/2003 |
| JP | 4071036 | B2 | 4/2008 |
| JP | 2009-247302 | A | 10/2009 |
| JP | 4359653 | B2 | 11/2009 |
| WO | 96/32840 | A1 | 10/1996 |
| WO | 97/12980 | A1 | 4/1997 |
| WO | 98/50422 | A1 | 11/1998 |
| WO | 2009031874 | A1 | 3/2009 |

OTHER PUBLICATIONS

Kloepper, Joseph W., "Induced Systemic Resistance and Promotion of Plant Growth by *Bacillus* spp.", Phytopathology, American Phytopathological Society, vol. 94, No. 11, US, Nov. 1, 2004, pp. 1259-1266.
Communication dated Sep. 23, 2014, from the European Patent Office in counterpart European Patent Application No. 12789590.2.
Huili Wang et al., "The inhibitory activity of endophytic *Bacillus* sp. strain CHM1 against plant pathogenic fungi and its plant growth-promoting effect", Crop Protection 2009, pp. 634-639, vol. 28.
Shazia Siddiqui et al., "Evaluation of fluorescent Pseudomonads and Bacillus isolates for the biocontrol of a wilt disease complex of pigeonpea", World Journal of Microbiology & Biotechnology 2005, pp. 729-732, vol. 21.
Alexandra Koumoutsi et al., "DegU and YczE Positively Regulate the Synthesis of Bacillomycin D by *Bacillus amyloliquefaciens* Strain FZB42", Applied and Environmental Microbiology, Nov. 2007, pp. 6953-6964, vol. 73, No. 21.
Xiao Hua Chen et al., "Comparative analyisis of the complete genome sequence of the plant growth-promoting bacterium Bacillus amyloliquefaciens FZB42", Nature Biotechnology, Sep. 2007, vol. 25, No. 9.
Li-Ting Wang et al., "Comparison of gyrB gene sequences, 16S rRNA gene sequences and DNA—DNA hybridization in the Bacillus subtilis group", International Journal of Systematic and Evolutionay Microbiology 2007, pp. 1846-1850, vol. 57.
S. Mignard et al., "16S rRNA sequencing in routine bacterial identification: A 30-month experiment", Journal of Microbiological Methods 2006, pp. 574-581, vol. 67.
International Search Report for PCT/JP2012/062935 dated Aug. 21, 2012.
Communication, dated Apr. 18, 2016, issued by the Intellectual Property Office of Israel in counterpart Patent Application No. 229514; English-language translation.

* cited by examiner

*Primary Examiner* — Renee Claytor
*Assistant Examiner* — Michelle F Paguio Frising
(74) *Attorney, Agent, or Firm* — Sughrue Mion, PLLC

(57) ABSTRACT

The present invention relates to the *Bacillus* sp. strains AT-332 (NITE BP-1095) and AT-79 (NITE BP-1094) isolated from nature; and a plant disease control agent, a nematode control agent and a plant growth promoter containing the strains as active bacteria. The *Bacillus* sp. strains AT-332 and AT-79 strain are effective in controlling both a wide range of various plant diseases and nematode-damage and capable of promoting the growth of useful plants, due to a culture containing a secondary metabolite of the strains or cultivated and isolated live bacteria of the strains being introduced to a plant body or to the culture soil.

8 Claims, 2 Drawing Sheets
(1 of 2 Drawing Sheet(s) Filed in Color)

(a) Non-treated  (b) Example 12  (c) Comparative Ex.1  (d) Comparative Ex.13

STRAIN BELONGING TO BACILLUS GENUS, MICROBIOLOGICAL AGENT, AND PLANT CULTIVATION METHOD

CROSS REFERENCE TO RELATED APPLICATIONS

This application is a National Stage of International Application No. PCT/JP2012/062935 filed May 21, 2012, claiming priority based on International Patent Application No. PCT/JP2011/062109 filed May 26, 2011, the contents of all of which are incorporated herein by reference in their entirety.

TECHNICAL FIELD

The present invention relates to a novel microorganism useful for controlling plant diseases and nematode damage and promoting the growth of plants. Specifically, the present invention relates to the *Bacillus* sp. strains AT-332 and AT-79, which are a novel microorganism exhibiting much superior effects in controlling plant diseases and nematode damage and promoting the growth of plants compared to microorganisms belonging to a closely-related *Bacillus amyloliquefaciens* disclosed in the literature; and a plant disease control agent, a nematode control agent and a plant growth promoter containing the fungus body and the culture of the microorganisms.

BACKGROUND ART

A main method for controlling plant diseases and nematodes is a method using chemical pesticides, and chemical pesticides have enabled stable production of crops to date. However, recently, it has become difficult to fully control the impact on the environment due to continuous use of chemical pesticides and emergence of drug-resistant bacteria by the conventional chemical pesticides; and diseases such as a bacterial disease which are difficult to control are developing into a major problem. Accordingly, biological control technology using a microorganism isolated from nature draws increasing attention and some of microorganism pesticides have been commercially-produced. However, the conventional microbiological pesticides have a defect that the effect is not stable and applicable diseases are fewer compared to chemical pesticides. In these circumstances, there has been growing demand for a novel microbiological pesticide which has new applicable diseases and exhibits a stable control effect.

As a plant disease control agent using a microorganism, a *Talaromyces flavus* agent, a *Pseudomonas fluorescens* agent, an avilurence *Erwinia carotovora* agent, a *Trichoderma atroiviride* agent, a *Bacillus simplex* agent, a *Bacillus subtilis* agent and the like are registered as a microbiological pesticide and have been used.

As a nematode control agent using a microorganism, a *Pasteuria penetrans* agent and a *Monacrosporium phymatophagum* agent are registered as a microbiological pesticide and have been used.

The specification of Japan Patent No. 2955655 (Patent Document 1) discloses a plant disease control agent using bacteria belonging to *Bacillus amyloliquefaciens*. The active ingredient of the plant disease control agent is the product of the microorganism and the bacteria per se are not used as a pesticide. Furthermore, the control target is a disease caused by filamentous bacteria and the document does not disclose the control of the bacterial disease. JP-A-2009-247302 publication (Patent Document 2) discloses a microorganism pesticide which can control the disease by filamentous bacteria and the bacterial disease at the same time in which viable bacteria cells per se are effective, but the document has no description on the nematode control.

The specification of Japan Patent No. 3471815 (Patent Document 3; WO 98/050422) discloses a plant disease control agent using *Bacillus* bacteria which can be used for a wide range of plant diseases and effective on corn rootworms, but the document has no description on the nematode control. The specification of Japan Patent No. 4071036 (Patent Document 4; US 2004/265292) discloses the *Bacillus* sp. D747 strain which can be used for controlling plant diseases and harmful insects, but the document has no description on the nematode control.

The specification of Japan Patent No. 3471811 (Patent Document 5; WO 96/032840) discloses a nematode control agent using *Bacillus* genus bacteria. The active ingredient of the nematode control agent is the bacteria or spore of the *Bacillus firmus* strain having an antinematode activity but the document has no description on the plant disease control. The specification of Japan Patent No. 4359653 (Patent Document 6; WO 1997/012980) discloses a method for controlling nematodes using a toxin produced by a novel *Bacillus thuringiensis* strain but the document has no description on the plant disease control.

In agriculture, chemical fertilizers are an important agricultural material which influences the yield of crops. However, 30 to 50% of the used chemical fertilizer components are not utilized in the crops but diffused in the environment, which causes eutrophication of rivers and groundwater contamination. A large quantity of fossil fuels is used in the production of chemical fertilizers and the production cost of the chemical fertilizers is increasing along with the soaring prices of fossil fuels. Furthermore, nitrogen oxide (NOx) as a decomposition product of a nitrogen fertilizer is said to be about 300 times more efficient in greenhouse emissions than carbon dioxide, and there is growing concern about global warming. Food shortage is expected in future due to the global population growth and therefore use of a material in order to increase the crop productivity is inevitable and there is growing need for a more environmentally-friendly material to replace the conventional chemical fertilizers.

In the light of such circumstances, studies have been made mainly on a broad range of *Rhizobium* bacteria, *Pseudomonas* bacteria and *Bacillus* bacteria. However, very few are in practical use because they are less effective.

As discussed above, no *Bacillus* bacterium which is effective on plant diseases in general, available in controlling nematodes and is effective in promoting plant growth has been known to date.

PRIOR ART DOCUMENTS

Patent Documents

Patent Document 1: Japan Patent No. 2955655
Patent Document 2: JP-A-2009-247302
Patent Document 3: Japan Patent No. 3471815
Patent Document 4: Japan Patent No. 4071036
Patent Document 5: Japan Patent No. 3471811
Patent Document 6: Japan Patent No. 4359653

DISCLOSURE OF INVENTION

Problem to be Solved by the Invention

An object of the present invention is to isolate a novel microorganism from nature to provide, which microorganism has effects of controlling multiple plant diseases, controlling nematodes and/or promoting plant growth.

Another object of the present invention is to provide a plant disease control agent, a nematode control agent and a plant growth promoter, which contain the above-mentioned microorganism as active bacteria and can be used as a biological pesticide (microbiological agent).

Means to Solve the Problem

As a result of intensive studies to solve the problem, the present inventors have succeeded in isolating a novel strain belonging to *Bacillus* genus from nature, which strain has effects of controlling multiple plant diseases, controlling nematodes and promoting plant growth, and accomplished the present invention.

The present invention relates to the strain described in 1 to 4 below, the microbiological agent in 5 to 8 below and the method for cultivating plants in 9 below.

1. A strain comprising 16S rDNA represented by the base sequence No. 2 or 3.
2. The strain as described in 1 above, wherein the strain per se and/or the culture of the strain shows effects of controlling plant diseases, controlling nematodes and/or promoting plant growth.
3. The *Bacillus* sp. AT-332 strain as described in 1 or 2 above, containing 16S rDNA represented by the base sequence No. 2.
4. The *Bacillus* sp. AT-79 strain as described in 1 or 2 above, containing 16S rDNA represented by the base sequence No. 3.
5. A microbiological agent containing the strain and/or the culture of the strain described in any one of 1 to 4 above as an active ingredient.
6. The microbiological agent as described in 5 above, which is a plant disease control agent.
7. The microbiological agent as described in 5 above, which is a nematode control agent.
8. The microbiological agent as described in 5 above, which is a plant growth promoter.
9. A method for cultivating plants, treating the plants with the microbiological agent described in any one of 5 to 8 above.

Effects of the Invention

The *Bacillus* sp. strains AT-332 and AT-79 of the present invention can control a wide range of various plant diseases and nematodes and further, can promote the growth of useful plants due to the culture (including viable bacteria cells) or cultivated and isolated live bacteria of the strains being introduced to a plant body such as roots, stems, leaves, seeds and fruits or to the culture soil.

BRIEF DESCRIPTION OF DRAWINGS

The patent or application file contains at least one drawing executed in color. Copies of this patent or patent application publication with color drawing(s) will be provided by the Office upon request and payment of the necessary fee.

MODE FOR CARRYING OUT THE INVENTION

Figure 1:
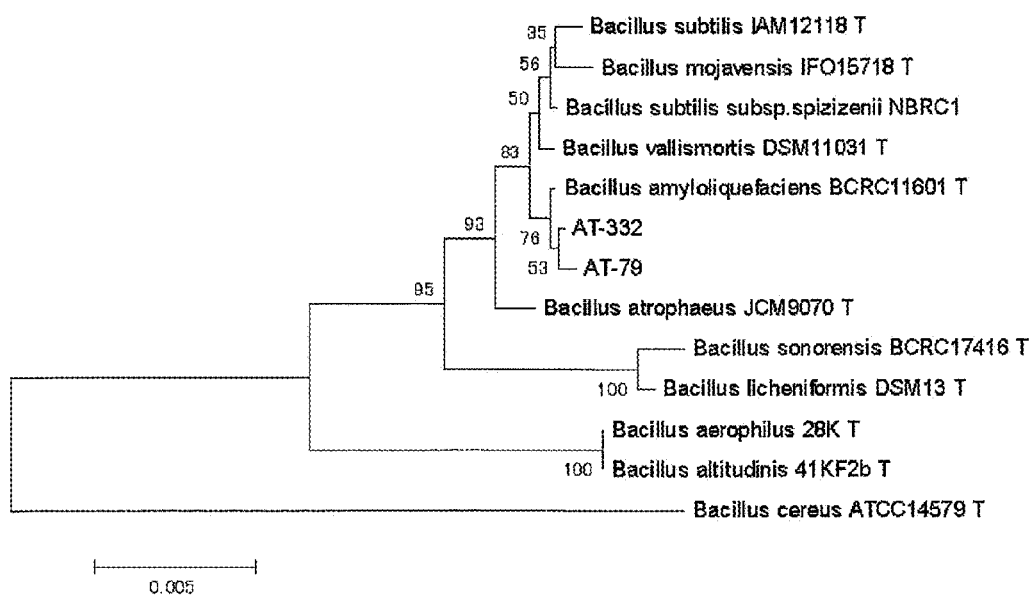
FIG. 1 shows the molecular phylogenetic tree using 16S rDNA base sequence of *Bacillus* sp. strains AT-332 and AT-79. In the figure, the numbers near the branches are the bootstrap values and a scale bar is shown at the lower left.

The present inventors screened for microorganisms from various plants, soils and the like for the purpose of newly developing a safe and superior microbial pesticide and/or microbial fertilizer which have a broad antibacterial spectrum against various plant diseases, show antinematode activity and have effect of promoting plant growth. As a result, the present inventors have made a useful finding that the strain isolated from the soil collected in Ibaraki Prefecture shows a broad antibacterial spectrum against various plant diseases, shows high insecticidal activity against nematodes and has effect of promoting plant growth.

The thus-newly-isolated both strains (AT-332 strain and AT-79 strain) are a gram-positive motile *bacillus* as is clear from the bacteriological characteristics to be described later, and grow and form spores under an aerobic condition. The both strains turned out positive in both of catalase reaction and oxidase reaction. Furthermore, as a result of identification based on the about 1500 bp-base sequence from the 5' terminal side of 16S rDNA, the strains were confirmed to be a novel strain belonging to *bacillus* genus related to *Bacillus amyloliquefaciens*. Due to the superior characteristics of having effects on a wide range of plant diseases, high control effect on nematodes and effect of promoting plant growth, the AT-332 and AT-79 strains were identified as a novel strain and designated as the *Bacillus* sp. AT-332 and AT-79 strains related to *Bacillus amyloliquefaciens*.

*Bacillus* sp. AT-332 strain and AT-79 strain of the present invention have been deposited as *Bacillus* sp. AT-332 and *Bacillus* sp. AT-79 strain with the depositary institution, Biological Resource Center, National Institute of Technology and Evaluation (2-5-8 Kazusakamatari, Kisarazu-shi, Chiba 292-0818 JAPAN) (original deposit date (accepted date): May 2, 2011; Accession number: NITE BP-1095 and NITE BP-1094).

The bacteriological characteristics of *Bacillus* sp. AT-332 (NITE BP-1095) are described below. The bacteriological characteristics have been determined in reference to the following documents.

PRIEST (F. G.), GOODFELLOW (M.), SHUTE (L. A.) and BERKELEY (R. C. W.): *Bacillus amyloliquefaciens* sp. nov., nom. rev. Int. J. Syst. Bacteriol., 1987, 37, 69-71 and Bergey's Manual of Systematic Bacteriology, Second Edition volume 3.

(1) Morphological Property
Form: rod-shaped bacterium
Size: width of 0.8 to 0.9 μm and length of 1.5 to 2.0 μm
Mobility: +
Epiphytic state of flagellum: peritrichous
Presence or absence of spores: +(quasi-terminal)
(2) Cultural Characteristics
Culture medium: nutrient agar medium (30° C.)
Form: circular
Prominence: flat
Periphery: entire margin
Surface status: smooth
Viscosity: viscous
Transparency: opaque
Color hue: cream color
Gloss: dull
Pigment production: non-productive (3) Physiological Characteristics
Gram staining: +
Nitrate reduction: −
Nitrogen desorption reaction: −
MR test: −
VP test: +
Indole generation: −
Hydrogen sulfide generation: −
Hydrolysis of starch: +
Use of citric acid: −(Koser)
　+(Christensen)
Use of inorganic nitrogen source: −(nitrate)
　+(ammonium salt)
Urease: −
Oxidase: +
Catalase: +
Range for growth pH 5: +
　pH 8: +
　pH 9: +
Temperature for growth 37° C.: +
　45° C.: +
　50° C.: +
　55° C.: −
Growth in anaerobic condition: −
OF test (oxidation/fermentation): −/−
Acid production/gas production from sugars:
　L-arabinose: +/−
　D-glucose: +/−
　D-fructose: +/−
　Maltose: +/−
　Lactose: −/−
　D-sorbitose: +/−
　Inositol: +/−
　D-xylose: +/−
　D-mannose: +/−
　D-galactose: −/−
　Saccharose: +/−
　Trehalose: +/−
　D-mannnitole: +/−
　Glycerin: +/−
β-galactosidase activity: −
Arginine dihydrolase activity: −
Lysine decarboxylase activity: −
Tryptophan deaminase activity: −
Gelatinase activity: +

The bacteriological characteristics of *Bacillus* sp. AT-79 (NITE BP-1094) are described below.

(1) Morphological Property
Form: rod-shaped bacterium
Size: width of 0.8 to 0.9 μm and length of 1.5 to 2.0 μm
Mobility: +
Epiphytic state of flagellum: peritrichous
Presence or absence of spores: +(quasi-terminal)

(2) Cultural Characteristics
Culture medium: nutrient agar medium (30° C.)
Form: circular
Prominence: flat
Periphery: entire margin
Surface status: smooth
Viscosity: viscous
Transparency: opaque
Color hue: cream color
Gloss: dull
Pigment production: non-productive (3) Physiological Characteristics
Gram staining: +
Nitrate reduction: −
Nitrogen desorption reaction: −
MR test: −
VP test: +
Indole generation: −
Hydrogen sulfide generation: −
Hydrolysis of starch: +
Use of citric acid: −(Koher)
　+(Christensen)
Use of inorganic nitrogen source: −(nitrate)
　+(ammonium salt)
Urease: −
Oxidase: +
Catalase: +
Range for growth pH 5: +
　pH 8: +
　pH 9: +
Temperature for growth 37° C.: +
　45° C.: +
　50° C.: +
　55° C.: −
Growth in anaerobic condition: −
OF test (oxidation/fermentation): −/−
Acid production/gas production from sugars:
　L-arabinose: +/−
　D-glucose: +/−
　D-fructose: +/−
　Maltose: +/−
　Lactose: −/−
　D-sorbitose: +/−
　Inositol: +/−
　D-xylose: +/−
　D-mannose: +/−
　D-galactose: −/−
　Saccharose: +/−
　Trehalose: +/−
　D-mannnitole: +/−
　Glycerin: +/−
β-galactosidase activity: −
Arginine dihydrolase activity: −
Lysine decarboxylase activity: −
Tryptophan deaminase activity: −
Gelatinase activity: +

The base sequences from the 5' terminal side of 16S rDNA of the *Bacillus* sp. AT-332 strain and AT-79 strain of the present invention are represented by sequence No. 2 and sequence No. 3, respectively.

Sequence No. 2 and sequence No. 3 differ from each other only in two bases at base No. 444 and base No. 1242. Base No. 444 is guanine (g) in sequence No. 2 and adenine (a) in sequence No. 3, and base No. 1242 is adenine (a) in sequence No. 2 and guanine (g) in sequence No. 3.

Therefore, the microorganism of the present invention is characterized in having the base sequence of sequence No. 1 including the above-mentioned sequences No. 2 and No. 3 (that is, base No. 444 and base No. 1242 are represented by "r") from the 5' terminal side of 16S rDNA.

In the present invention, the 16S rDNA base sequence was analyzed as below.

InstaGene Matrix (produced by BIO RAD Laboratories, Inc., California (CA), U.S.A.) was used for DNA extraction; PrimeSTAR HS DNA Polymerase (produced by Takara Bio Inc.) was used for PCR; BigDye Terminator v3.1 Cycle Sequencing Kit (produced by Applied Biosystems, California (CA), U.S.A.) was used to determine cycle sequence, respectively. The used primers (in accordance with "Gene Analysis Method—method for determining the base sequence of 16S rRNA gene", Yasuyoshi Nakagawa et al., edited by the Society for Actinomycetes Japan, Classification and identification of Actinomycetes, pp. 88-117, Business Center for Academic Societies Japan, 2001) were 9F, 339F, 785F, 1099F, 536R, 802R, 1242R and 1541R. The sequence was identified using ABI PRISM 3100 Genetic Analyzer System (produced by Applied Biosystems, California (CA), U.S.A.).

As a result of homology search on the basis of the international base sequence database (GenBank/DDBJ/EMBL) using BLAST (ALTSCHUL, (S.F.) et al., Gapped BLAST and PSI-BLAST: a new generation of protein database search programs. Nucleic Acid Res. 1997.25, 3389-3402), the base sequence of 16S rDNA of AT-332 strain and AT-79 strain had high degree of homology with the 16S rDNA derived from *Bacillus* genus, and both of the strains had the highest homology of 99.9% with 16S rDNA of *Bacillus amyloliquefaciens* BCRC11601 strain. On the other hand, as a result of the homology search on the basis of the international base sequence database (GenBank/DDBJ/EMBL), no 16S rDNA base sequence of AT-332 and AT-79 strains did exactly match the 16S rDNA base sequence derived from *Bacillus* genus.

In the present invention, molecular phylogenetic analysis was performed as below.

16S rDNA derived from the standard strain from the strain group which was assumed to be closely-related was obtained from the international base sequence database (GenBank/DDBJ/EMBL) to perform molecular phylogenetic analysis using 1500 bp of the 16S rDNA base sequence obtained in the above.

16S rDNA used for the molecular phylogenetic analysis were derived from the following strains.

*Bacillus subtilis*, IAM12118T (AB042061)
*Bacillus subtilis* subsp. spizizenii, NBRC101239T (AB325584)
*Bacillus mojavensis*, IFO15718 T (AB021191)
*Bacillus vallismortis*, DSM11031 T (AB021198)
*Bacillus amyloliquefaciens*, BCRC11601 T (EF433406)
*Bacillus atrophaeus*, JCM9070 T (AB021181)
*Bacillus aerophilus*, 28K T (AJ831844)
*Bacillus sonorensis*, BCRC17416 T (EF433411)
*Bacillus licheniformis*, DSM13 T (AE017333)
*Bacillus altitudinis*, 41KF2b T (AJ831842)
*Bacillus cereus* ATCC14579 T (NC_004722)BSL2

"T" at the end of the strain name means the standard strain of the species. BSL means that the strain is at a bio safety level (level 2 or higher is indicated). The codes in the brackets indicate the accession number.

The obtained molecular phylogenetic tree is shown in FIG. 1.

The numbers near the branches are the bootstrap values and a scale bar is shown at the lower left.

Since AT-332 strain and AT-79 strain have the property that does not carry out nitrate reduction as mentioned above, their mycological characteristics did not exactly match those of the *Bacillus amyloliquefaciens* described in Bergey's Manual. Also, from the result of the 16S rDNA analysis, the AT-332 strain and AT-79 strain are considered to be closely related to *Bacillus amyloliquefaciens* but cannot be identified as *Bacillus amyloliquefaciens* and AT-332 strain and AT-79 strain was determined to be a novel strain belonging to *Bacillus* genus.

The *Bacillus* sp. AT-332 strain and AT-79 strain of the present invention are allowed to grow by known means such as the static culture on a solid medium and the liquid culture and the kind of the available medium, culture conditions and the like are not particularly limited as long as they allow the bacteria to survive and grow. Examples of the medium include a medium containing glucose, peptone, yeast extract and the like as well as a general medium such as a meat extract. Also, other than a liquid medium, a solid medium such as an agar slant medium and a plate medium other than a liquid medium may be used.

All the carbon sources which the AT-332 strain and AT-79 strain can utilize can be used for the medium. Specific examples include various synthetic or natural carbon sources which the AT-332 strain and AT-79 strain can utilize other than sugars such as glucose, galactose, lactose, sucrose, maltose, malt extracts, waste molasses, starch syrup and starch hydrolysate.

Similarly, various synthetic and natural substances which the above-mentioned strains can utilize such as an organic nitrogen-containing substance including peptone, meat extract, yeast extract, soy-bean powder and corn steep liquor can be used for the nitrogen source of the medium.

According to a conventional method for culturing microorganisms, inorganic salts such as dietary salt and phosphoric salt, salts of metal such as calcium, magnesium and iron and micronutrients such as vitamins and amino acids can be added as needed.

The culture can be performed under an aerobic condition such as the shake culture and aeration culture. The culture temperature is 20 to 40° C. and preferably 25 to 35° C., pH is 5 to 8 and preferably 6 to 7, and the culture period is one to four days and preferably two to three days.

The culture containing the bacterial body of the *Bacillus* sp. AT-332 strain and AT-79 strain of the present invention has the property of controlling various plant diseases, controlling nematodes and promoting growth of useful plants.

Various plant diseases can be prevented and nematodes can be controlled by allowing the processed product of the culture containing the bacterial body of the *Bacillus* sp. AT-332 strain and AT-79 strain of the present invention, mixture of the culture and other components and the like; the processed product of separated cultured bacteria cells obtained by subjecting the culture product to centrifugal separation treatment or by washing the bacteria cells, the mixture of separated cultured bacteria cells and other components, and the like; a diluent thereof with a liquid or a solid and the like to exist on the plant body such as roots, stems, leaves, seeds and fruits or in the grove soil.

The *Bacillus* sp. AT-332 strain and AT-79 strain of the present invention is available as a plant disease control agent, a nematode control agent and a plant disease promoter in any state of nutritive cells, spores or the mixture of both as long as the bacteria are living. Also, the strains can be used if the components of the culture medium are mixed as they are after the cultivation or if they are in a state where the components other than bacteria cells are removed by washing with distilled water and the like.

The *Bacillus* sp. AT-332 strain and AT-79 strain of the present invention can control the plant disease caused by fungi and bacteria belonging to Oomycetes, Ascomycetes, Basidiomycetes and Deuteromycetes depending on the type of application and can control phytoparasitic nematode such as *Ditylenchus dipasaci*, *Ditylenchus destructor*, *Pratylenchus* sp., *Meloidogyne* sp., *Heterodera* sp. and *Globodera* spp. The strains can promote the growth of crops, vegetables, fruits, flowers and legumes at the same time.

Specifically, the offending bacteria which the *Bacillus* sp. AT-332 strain and AT-79 strain of the present invention can control include *Pyricularia oryzae*, *Cochliobolus miyabeanus*, *Rhizoctonia solani* and *Gibberella fujikuroi* which infest rice; *Erysiphe graminis* f. sp. *hordei*, *Erysiphe*

*graminis* f. sp. *tritici*, *Puccinia striiformis*, *Puccinia graminis*, *Puccinia recondita* f. sp. *tritici*, *Puccinia hordei*, *Gibberella zeae*, *Pyrenophorateres*, *Typhula incarnata*, *Typhula ishikariensis*, *Sclerotiniaborealis*, *Micronectriella nivalis*, *Ustilago nuda*, *Tilletia caries*, *Tilletia toetida*, *Tapesia yallundea, Phynchosporium secalis* f. sp. *hordei, Septoria tritici* and *Lentosphaeria nodorum* which infest wheats; *Diaporthe citri, Elsinoe fawcettii, Phytophthora citrophthora, Penicillium digitatum* and *Penicillium italicum* of citrus plants; *Monilinia mali, Valsa ceratosperma, Podosphaera leucotricha, Alternaria alternata* apple pathotype, *Venturia inaequalis, Gymnosporangium yamadae, Botriophaeria berengeriana* f. sp. *piricola, Zygophiala jamaicensis, Gloeodes pomigena, Mycosphaerella pomi, Glomerella cingulata* and *Diplocarponmali* of apples; *Venturia nashicola, Alternaria alternata* japanese pear pathotype, *Physalospora piricola* and *Gymnosporangium asiaticum* of pears; *Monilinia fructicola, Cladosporium carpophilum* and *Phomopsis* sp. of peaches; *Pseudocercospora vitis, Marssonina viticola, Elsinoe ampelina, Glomerella cingulata, Uncinula necator, Phakopsora ampelopsidis* and *Phomopsis* sp. of grapes; *Phyllactinia kakicola, Colletotrichum gloeosporioides, Cercospora kaki* and *Mycosphaerella nawae* of persimmons; *Cladosporium carpophilum* of plums; *Monilinia fructicola* of *Prunus avium; Sphaerotheca fuliginea, Didymella bryoniae, Colletotrichum legenarium* of gourds; *Alternaria solani, Cladosporium fulvum* of tomatoes; *Phomopsis vexans* and *Erysiphe cichoracearum* of eggplants; *Alternaria japonica, Alternaria bracicae, Alternaria brassicicola* and *Cercosporella brassicae* of *brassica* vegetables; *Pucciniaallii* of green onions; *Pyrhium ultimum* and *Pythium zigiberis* of gingers; *Sphaerotheca humuli* and *Glomerella cingulata* of strawberries; *Cercospora kikuchii, Elsinoe glycines* and *Diaporthe phaseolorum* var. *sojae* of soybeans; *Cercospora canescens* and *Uromyces phaseoli* var. *azukicola* of azuki beans; *Colletotrichum lindemuthianum* of marrow beans; *Cercosporidium personatum, Cercospora arachidicola* and *Shaceloma arachidis* of peanuts; *Erysiphe pisi* of peas; *Alternaria solani* of potatoes; *Exobasidium reticulatum, Elsinoe leucospila, Pestalotiopsis theae* and *Pestalotiopsis longiseta* of teas; *Alternaria longipes, Erysiphe cichoracearum* and *Colletotrichum gloeosporioides* of tobaccos; *Cercospora beticola* of sugar beets; *Curvularia geniculata* and *Ceratobasidium* spp. of the lawn grass; *Diplocarpon rosae* and *Shaerotheca pannosa* of roses; *Septoria obesa* and *Puccinia horiana* of chrysanthemums; and *Botrytis cinerea* and *Sclerotinia sclerotiorum* of various crop plants, but not limited thereto.

The plant disease control agent of the present invention includes a postharvest disease control agent for the stored crops after harvesting, particularly in order to prevent fruits and the like from decay. There is no limit on the kinds of crops to which the postharvest disease control agent of the present can be applied, and examples include fruits such as strawberry, grape, fig, citrus, peach, melon, watermelon, apple, pear, banana and pineapple and vegetables such as a cucumber, tomato, Chinese cabbage, cabbage, Welsh onion, onion, carrot, Japanese radish, ginger, green pepper, eggplant, pumpkin and bean sprout. There is no limit on the kinds of fungi which cause the postharvest disease and examples include *Botrytis cinerea, Colletotrichum gloeosporioides* and *Alternaria alternata.*

Examples of nematodes which the *Bacillus* sp. AT-332 strain and AT-79 strain of the present invention can control include *Meloidogyne* sp. such as *Meloidogyne hapla, Meloidogyne incognita, Meloidogyne javanica* and *Meloidogyne* species; *Globodera* spp. such as *Globodera rostochiensis* and other *Globodera* species; *Heterodera* sp. such as *Heterodera avenae, Heterodera glycines, Heterodera schachtii, Heterodera trifolii* and other *Heterodera* species; *Anguiana* species belonging to *Anguina funesta; Aphelenchoides* species; *Belonolaimus longicaudatus* and other species belonging to *Belonolaimus; Bursaphelenchus xylophilus* belonging to *Bursaphelenchus xylophilus* and other *Bursaphelenchus* species; *Criconema* species, *Criconemella* species, *Criconemoides* species and *Mesocriconema* species belonging to *Criconemoides; Ditylenchus* destructor, *Ditylenchus dipsaci* and other species belonging to *Ditylenchus; Dolichodorus* species belonging to awl nematodes; *Heliocotylenchus multicinctus* belonging to *Helicotylenchus* and other *Helicotylenchus* species; *Hemicycliophora* species and *Hemicriconemoides* species belonging to sheath and sheathoid nematodes; *Hirshmanniella* species; *Hoploaimus* species belonging to *Hoplolaimus; Nacobbus* species belonging to *Nacobbus; Longidorus elongatus* belonging to *Longidorus* and other *Longidorus* species; *Pratylenchus neglectus, Pratylenchus penetrans, Pratylenchus curvitatus, Pratylenchus goodeyi* and other *Pratylenchus* species belonging to *PratyLenchus* sp.; *Radopholus similis* and other species belonging to *Radopholus; Rotylenchus robustus* and other *Rotylenchus* species belonging to *Rotylenchulus reniformis; Scutellonema* species; *Trichodorus primitivus* and other *Trichodorus* species belonging to stubby root nematodes; *Paratrichodorus* species; *Tylenchorhynchus claytoni, Tylenchorhynchus dubius* and other species belonging to *Tylenchorhynchus; Tylenchulus* species belonging to *Tylenchulus semipenetrans*; and *Xiphinema* species belonging to *Xiphinema americanum*, but not limited thereto.

The *Bacillus* sp. AT-332 strain and AT-79 strain of the present invention are especially useful for controlling *Meloidogyne* species, *Globodera* species, *Heterodera* species, *Pratylenchus* species, *Radopholus* species, *Rotylenchus* species and *Tylenchulus* species, and in particular can be suitably used for exterminating *Meloidogyne* species, *Pratylenchus species, Globodera species* and *Heterodera* species.

Examples of crops which the *Bacillus* sp. AT-332 strain and AT-79 strain of the present invention can promote growth include cereal crops such as rice, wheat and corn; vegetables such as carrot, cucumber, Japanese radish, pumpkin, lettuce, eggplant, tomato, cabbage, potato, Chinese cabbage, crown daisy, Japanese mustard spinach, green pepper, Welsh onion, onion, ginger, garlic, strawberry; mushrooms such as shiitake mushroom; fruit trees such as persimmon, pear, orange, grape, apple and peach; flowers and ornamental plants such as chrythansemum, tulip and rose; and legumes such as soybean, sesame and peanut.

The plant disease control agent, nematode control agent and plant growth promoter of the present invention contains the *Bacillus* sp. AT-332 strain and AT-79 strain which can control the plant diseases and nematodes and have an effect of promoting plant growth as mentioned above as an indicated microorganism.

In the plant disease control agent, nematode control agent and plant growth promoter of the present invention, the AT-332 strain or AT-79 strain can be used singly or in combination. Also, the mutant of each of the strains can be used. The mutant is the one that possesses the above-mentioned bacteriological property of the AT-332 strain and AT-79 and an activity of controlling the plant diseases, controlling nematodes and promoting plant growth. A natural mutant strain, a mutant strain caused by ultraviolet ray or a chemical mutagensis agent, a cell fusion strain and a genetically-modified strain or the like can be used.

When the live bacteria of the AT-332 strain and AT-79 strain are used in the plant disease control agent, nematode control agent and plant growth promoter of the present invention, it is preferable to add the bacteria to the plant body at a concentration of $10^5$ to $10^{10}$ units/ml.

When the culture product of the AT-332 strain and/or AT-79 strain is used, the dosage can be appropriately determined in individual cases of the above-mentioned viable bacteria.

As the microbiological agent (plant disease control agent, nematode control agent and plant growth promoter) of the present invention, the bacteria cells and/or culture product of the AT-332 strain and AT-79 strain can be used singly. Or the microbiological agent can be diluted with an inert liquid or a solid carrier to be used as a pharmacological agent with addition of the surfactant, dispersing agent and other adjuvant as needed. Examples of specific formulation include granular formulation, dust formulation, wettable powder, suspension agent and emulsion formulation.

Examples of the carrier include talc, bentonite, kaolin, clay, diatom earth, white carbon, vermiculite, lime hydrate, ammonium sulfate, silica sand, urea, a porous solid carrier and liquid carriers such as water, isopropyl alcohol, methyl naphthalene, xylene, cyclohexanone and alkylene glycol. Examples of the surfactant and dispersion agent include dinaphthylmethanesulfonic acid salts, alcohol sulfuric acid ester salts, lignin sulfonic acid salts, alkylarylsulfonic acid salts, polyoxyethylene glycol ethers, polyoxyethylene sorbitan monoalkylate and polyoxyethylene alkylaryl ethers. Examples of the adjuvant include carboxymethylcellulose, polyethylene glycol, propylene glycol, gum Arabic and xanthan gum; and examples of the cryoprotective agent include skim milk and pH buffering agent. The amount of the live bacteria and/or culture product of the AT-332 strain and AT-79 strain, the time of application and the application amount can be appropriately determined depending on each case of the above viable bacteria.

The microbiological agent (plant disease control agent, nematode control agent and plant growth promoter) of the present invention can contain active ingredients other than those of the present invention: i.e. insecticides, other bactericidal agents, herbicides, plant growth regulators and fertilizers. Also, the plant disease control agent, nematode control agent and plant growth promoter of the present invention may contain the strain of other species in combination with the AT-332 strain and/or AT-79 strain.

Examples of the bactericidal components include bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole, oxypoconazole fumaric acid, himexazole, azoxystrobin, dimoxystrobin, enestroburin, fluoxastrobin, kresoxym-methyl, metominostrobin, oryzastrobin, picoxystrobin, pyraclostrobin, trifloxystrobin, carboxin, benalaxyl, boscalid, bixafen, fenhexamid, flutolanil, furametpyr, mepronil, metalaxyl, mefenoxam, ofurace, oxadixyl, oxycarboxin, penthiopyrad, thifluzamide, tianidil, dimethomorph, flumorph, flumetover, fluopicolide, carpropamid, diclocymet, mandipropamid, fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, anilazine, diclomezine, pyroquilon, proquinazid, tricyclazole, captafol, captan, dazomet, folpet, fenoxanil, quinoxyfen, amisulbrom, manzeb, maneb, metam, metiram, ferbam, propineb, thiuram, zineb, ziram, diethofencarb, iprovalicarb, benthiavalicarb-isopropyl, propamocarb hydrochloride, thiophanate methyl, pyribencarb, Bordeaux mixture, basic copper chloride, basic copper sulfide, cupric hydroxide, copper 8-hydroxyquinoline, dodine, iminoctadine albesilate, iminoctadine acetate, guazatine, kasugamycin, streptomycin, polyoxin, oxytetracycline, validamycin A, binapacryl, dinocap, dinobuton, dithianon, isoprothiolane, edifenphos, iprobenfos, fosetyl, fosetyl aluminum, pyrasophos, tolclofos-methyl, chlorothalonil, dichlofluanid, flusulfamide, hexyachlorobenzene, phthalide, pencycuron, quintozene, cyflufenamid, cymoxanil, dimethirimol, ethyrimol, furalaxyl, metrafenone, spiroxamine, amobam, sulfur, lime sulfur, echlomezole, potassium bicarbonate, calcium bicarbonate, thiadiazine, tecloftalam, triazine, copper nonylphenol sulfonate, hydroxy isoxazole, fluoroimide, polycarbamate, methasulfocarb, EDDP, IBP, tolfenpyrad, fluopyram, isotianil and isopyrazam, but not limited thereto.

Examples of the insecticidal components include acetamiprid, pymetrozine, fenitrothion, acephate, carbaryl, methomyl, cartap, cyhalothrin, ethofenprox, teflubenzuron, flubendiamide, flufenoxuron, tebufenozide, fenpyroximate, pyridaben, imidacloprid, buprofezin, BPMC, MIPC, malathion, methidathion, fenthion, daiazinon, oxydeprofos, vamidothion, ethiofencarb, pirimicarb, permethrin, cypermethrin, bifenthrin, halfenprox, silafluofen, nitenpyram, chlorfluazuron, methoxyfenozide, tebufenpyrad, pyrimidifen, kelthane, propargite, hexythiazox, clofentezine, spinosad, milbemectin, BT (*Bacillus thuringiensis*), indoxacarb, metaflumizone, chlorfenapyr, fipronil, etoxazole, acequinocyl, pirimiphos-methyl, acrinathrin, quinomethionate, chlorpyrifos, abamectin, emamectin benzoate, fenbutatin oxide, terbufos, ethoprophos, cadusafos, fenamiphos, fensulfothion, DSP, dichlofenthion, fosthiazate, oxamyl, isoamidofos, fosthietan, isazophos, thionazin, benfuracarb, spirodiclofen, ethiofencarb, azinphos-methyl, disulfoton, methiocarb, oxidemethon-methyl, parathion, cyfluthrin, beta-cyfluthrin, tebupirimfos, spiromesifen, endosulfan, amitraz, tralomethrin, acetoprole, ethiprole, ethion, triclorfon, methamidophos, dichlorvos, mevinphos, monocrotophos, dimethoate, formetanate, formothion, mecarbam, thiometon, naled, methyl parathion, cyanophos, diamidafos, albendazole, oxibendazole, fenbendazole, oxfendazole, propaphos, sulprofos, prothiofos, profenofos, isofenphos, temephos, phenthoate, dimethylvinphos, chlorfenvinphos, tetrachlorvinphos, phoxim, isoxathion, pyraclofos, chlorpyrifos, pyridaphenthion, phosalone, phosmet, dioxabenzofos, quinalphos, pyrethrin, allethrin, prallethrin, resmethrin, permethrin, tefluthrin, fenpropathrin, alpha-cypermethrin, lambda-cyhalothrin, delta-methrin, fenvalerate, esfenvalerate, flucythrinate, fluvalinate, cycloprothrin, thiodicarb, aldicarb, alanycarb, metolcarb, xylylcarb, propoxur, fenoxycarb, fenothiocarb, bifenazate, carbofuran, carbosulfan, sulfur, pyrifluquinazon, furathiocarb, diafenthiuron, diflubenzuron, hexaflumuron, novaluron, lufenuron, chlorfluazuron, triclohexyltin hydroxide, sodium oleate, potassium oleate, methoprene, hydroprene, binapacryl, chlorbenzilate, phenisobromolate, tetradifon, bensultap, benzomate, chromafenozide, halofenozide, endosulfan, diofenolan, tolfenpyrad triazamate, nicotine sulfate, thiacloprid, thiamethoxam, clothianidin, dinotefuran, fluazinam, pyriproxyfen, fluacrypyrim, hydramethylnon, cyromazine, TPIC, thiocyclam, fenazaquin, polynactin complex, azadirachtin, rotenone, hydroxypropyl starch, mesulfenphos, phosphocarb, aldoxycarb, metham sodium, morantel tartrate, dazomet, levamisole hydrochloride, trichlamide, pyridalyl, chlorantraniliprole, cyenopyrafen and cyflumetofen, but not limited thereto.

The plant disease control agent, nematode control agent and plant growth promoter of the present invention can be directly applied as they are or applied as a solution diluted with water and the like. The application method of the plant disease control agent, nematode control agent and plant growth promoter of the present invention is not particularly limited and examples thereof include a method of spraying the agent directly on plants and insect pests, a method of spraying the agent on the soil, a method of adding the agent to the water and fertilizer to be applied on plants and the soil and a method of coating the seeds with the agent. In addition, it is desirable to appropriately adjust the application amount of the drug product since the application amount varies depending on the disease and the insect pest to be controlled, the crops as the subject of the application, the application method, occurrence tendency of diseases, degree of the damage, environmental conditions and the formulations to be used.

As discussed above, the AT-332 strain and AT-79 strain of the present invention have a broad disease and nematicidal spectrum and can control various kinds of plant diseases and nematodes, and can promote plant growth. Since the plant disease control agent, nematode control agent and plant growth promoter of the present invention comprising these strains are highly safe for the environment and has control effects on various kinds of diseases and nematodes, the plant disease control agent can prevent a wide range of diseases and nematodes without using other means in combination and can be used as a biological pesticide and/or biological fertilizer which can promote the growth of useful plants as well.

EXAMPLES

The present invention is to be described in more details with Production Example, Formulation Examples, Examples and Comparative Examples, but the present invention is not limited to these examples.

Culture of AT-332 strain and AT-79 strain

The AT-332 strain and AT-79 strain were isolated from the soil containing plant roots.

In detail, 1 g of a dry soil obtained by collecting the soil in Moriya City in Ibaraki Prefecture, Japan in August 2009 and subjecting it to heat treatment (80° C., for 10 minutes) was suspended in the sterilized water. The suspension was diluted with the dilution rate of $10^2$ to $10^4$ times and the separate culture of the suspension was carried out on the nutrient broth medium (Eiken Chemical Co., Ltd.) (28° C., for three days) and the formed colonies were isolated. The isolated colonies were cultured on a potato dextrose agar medium and the strains effective against pathogens of various plant diseases were found. The strains were further subjected to shaking culture on a potato dextrose liquid medium, and the *Bacillus* sp. AT-332 strain and AT-79 strain were isolated as a strain having an activity against the second-stage larva of sweetpotato *Meloidogyne* sp.

The method for identification of each of the strains, the various analysis methods and results thereof, and bacteriological properties are those as described in "Mode for Carrying out the Invention".

Production Example 1

Cultivation and Preparation of AT-332 Strain

As a preculture, one loopful of the preserved bacteria of the present invention (AT-332 strain) was inoculated on 60 ml per flask of a nutrient broth medium (available from Eiken Chemical Co., Ltd.) in a 500 ml conical flask with baffles, and subjected to shaking culture using a rotary shaker at 180 rpm and 28° C. for one day.

60 ml of the culture obtained by the above preculture was inoculated in a jar fermentor with a 5000 ml volume containing a 2,000 ml of LB medium (20 g of peptone, 10 g of yeast extract, 20 g of sodium chloride and water for the rest) and cultivated as the main culture at 500 rpm, aeration rate of 1 l/hour and 35° C. for three days.

About 1,800 g of culture was obtained by the above main culture. The concentration of the bacteria cell was about $8.0 \times 10^9$ CFU/ml.

About 140 g of dry powder was obtained by freezing 1,800 g of the obtained culture product at −80° C., followed by freeze-drying under reduced pressure and pulverization. The bacteria cell concentration of the powder was about $1.0 \times 10^{11}$ CFU/g.

Production Example 2

Cultivation and Preparation of AT-79 Strain

As a preculture, one loopful of the preserved bacteria of the present invention (AT-79 strain) was inoculated on 60 ml per flask of a nutrient broth medium (available from Eiken Chemical Co., Ltd.) in a 500 ml conical flask with baffles, and subjected to shaking culture using a rotary shaker at 180 rpm and 28° C. for one day.

60 ml of the culture obtained by the above preculture was inoculated in a jar fermentor with a 5000 ml volume containing a 2,000 ml of LB medium (20 g of tryptone, 10 g of yeast extract, 20 g of sodium chloride and water for the rest) and cultivated as the main culture at 500 rpm, aeration rate of 1 l/hour and 35° C. for three days.

About 1,700 g of culture was obtained by the above main culture. The bacteria cell concentration of the powder was about $9.0 \times 10^9$ CFU/g.

About 130 g of dry powder was obtained by freezing 1,700 g of the obtained culture product at −80° C., followed by freeze-drying under reduced pressure and pulverization. The bacteria cell concentration of the powder was about $1.0 \times 10^{11}$ CFU/g.

Formulation Examples are given below. Here, the word "part(s)" means a part(s) by mass.

Formulation Example 1

Wettable Powder 60 parts of dry powder obtained by Formulation Example 1, 25 parts of diatom earth, 5 parts of white carbon, 8 parts of lignin sulfonate and 2 parts of alkyl naphthalene sulfonate were mixed and pulverized to thereby obtain wettable powder.

Formulation Example 2

Granular Formulation 5 parts of dry powder obtained by Formulation Example 1, 25 parts of bentonite, 66 parts of talc, 2 parts of dodecylbenzene sulfonate and 2 parts of lignin sulfonate were mixed and pulverized. After adding about 20 parts of water thereto and kneading the mixture by a kneading machine, the resultant was granulated by a granulator and dried, and then the size of the granules was regulated to obtain a granular formulation.

Formulation Example 3

Wettable Powder 60 parts of dry powder obtained by Formulation Example 2, 25 parts of diatom earth, 5 parts of white carbon, 8 parts of lignin sulfonate and 2 parts of alkyl naphthalene sulfonate were mixed and pulverized to thereby obtain wettable powder.

Formulation Example 4

Granular Formulation 5 parts of dry powder obtained by Formulation Example 2, 25 parts of bentonite, 66 parts of talc, 2 parts of dodecylbenzene sulfonate and 2 parts of lignin sulfonate were mixed and pulverized. After adding about 20 parts of water thereto and kneading the mixture by a kneading machine, the resultant was granulated by a granulator and dried, and then the size of the granules was regulated to obtain a granular formulation.

Next, Examples and Comparative Examples for testing the effects of the plant disease control agent, nematode control agent and plant growth promoter of the present invention are described below.

Example 1 and Comparative Example 1

Test for the Effects Against Rice Blast

Sufficient doses of the diluted wettable powders in Formulation Examples 1 and 3 with the dilution rate of 250 times was sprayed with a spray gun on the rice (variety: Koshihikari, 15 plants per hill) grown in a glasshouse to the third-leaf unfolding stage in a plastic pot 6 cm in diameter. As a comparative example, the Impression wettable powder (produced by SDS Biotech K.K.) with the dilution rate of 250 times was also subjected to the test in the same manner. The next day, suspension of the rice blast pathogen (*Pyricularia oryzae*) spores was sprayed and inoculated. After retaining the pots in a humidity room at 22° C. for 24 hours, the pots were allowed to stand in greenhouse for seven days and the number of lesions in the inoculated leaves was investigated to thereby determine the control titer. The control titer (%) was calculated on the basis of the number of lesions of the leaves in the non-treated region. As can be seen from the results shown in Table 1, by the treatment with the microbiological agent of the present invention, the incidence of rice blast was greatly reduced compared to the non-treated region, and significantly high control effects were obtained.

TABLE 1

|  | Number of lesions | Control titer (%) |
|---|---|---|
| Treated region (Formulation Example 1) | 28 | 86.0 |
| Treated region (Formulation Example 3) | 20 | 90.0 |
| Comparative region (Impression wettable powder) | 85 | 57.5 |
| Non-treatment region | 200 | 0.0 |

Example 2 and Comparative Example 2

Test for the Effects on Cucumber Anthracnose

Sufficient doses of the wettable powders in Formulation Examples 1 and 3 with the dilution rate of 250 times were sprayed by a spray gun on the first and second leaves of cucumbers (variety: Tokiwa Hikari No. 3 p-type) grown in a glasshouse to the third-leaf unfolding stage in a plastic pot 6 cm in diameter. As a comparative example, the diluent of Impression wettable powder (produced by SDS Biotech K.K.) with the dilution rate of 250 times was also subjected to the test in the same manner. The next day, suspension of the cucumber *Colletorichum lagenarium* spores was sprayed and inoculated. After retaining the pots in a humidity room at 22° C. for 24 hours, the pots were allowed to stand in greenhouse for seven days and the diseased area rate in the first and second leaves was investigated with eyes to thereby determine the control titer. The control titer (%) was calculated on the basis of the diseased area rate in the non-treatment region. As can be seen from the results in Table 2, by the treatment with the microbiological agent of the present invention, the incidence of cucumber *Colletorichum lagenarium* was greatly reduced compared to the non-treated region, and significantly high control effects were obtained.

TABLE 2

|  | Diseased area rate | Control titer (%) |
|---|---|---|
| Treated region (Formulation Example 1) | 7 | 82.5 |
| Treated region (Formulation Example 3) | 8 | 80.0 |
| Comparative region (Impression wettable powder) | 25 | 37.5 |
| Non-treatment region | 40 | 0.0 |

Example 3 and Comparative Example 3

Test for the Effects on Tomato *Phytophthora infestans*

Sufficient doses of the wettable powders in Formulation Examples 1 and 3 with the dilution rate of 250 times were sprayed by a spray gun on the tomatoes (variety: Sugar lump) grown in a glasshouse to the fifth-leaf unfolding stage in a plastic pot 6 cm in diameter. As a comparative example, the diluent of Impression wettable powder (produced by SDS Biotech K.K.) with the dilution rate of 250 times was also subjected to the test in the same manner. The next day, suspension of the tomato *Phytophthora infestans* zoospores was sprayed and inoculated. After retaining the pots in a humidity room at 22° C. for 16 hours, the pots were allowed to stand in greenhouse for three days and the diseased area rate in the third, fourth and fifth leaves was investigated with eyes to thereby determine the control titer. The control titer (%) was calculated on the basis of the diseased area rate in the non-treatment region. As can be seen from the results in Table 3, by the treatment with the microbiological agent of the present invention, the incidence of tomato *Phytophthora infestans* was greatly reduced compared to the non-treated region, and significantly high control effects were obtained.

TABLE 3

|  | Diseased area rate | Control titer (%) |
| --- | --- | --- |
| Treated region (Formulation Example 1) | 7 | 84.4 |
| Treated region (Formulation Example 3) | 6 | 86.7 |
| Comparative region (Impression wettable powder) | 40 | 11.1 |
| Non-treatment region | 45 | 0.0 |

Example 4 and Comparative Example 4

Test for the Effects on Cucumber *Pseudoperonospora cubensis*

Sufficient doses of the wettable powders in Formulation Examples 1 and 3 with the dilution rate of 250 times were sprayed by a spray gun on the cucumbers (variety: Hikari No. 3 p-type) grown in a glasshouse to the third-leaf unfolding stage in a plastic pot 6 cm in diameter. As a comparative example, the diluent of Impression wettable powder (produced by SDS Biotech K.K.) with the dilution rate of 250 times was also subjected to the test in the same manner. The next day, suspension of the cucumber *Pseudoperonospora cubensis* zoospores was sprayed and inoculated. After retaining the pots in a humidity room at 22° C. for 18 hours, the pots were allowed to stand in greenhouse for three days and the diseased area rate in the first and second leaves was investigated with eyes to thereby determine the control titer. The control titer (%) was calculated on the basis of the diseased area rate in the non-treatment region. As can be seen from the results in Table 4, by the treatment with the microbiological agent of the present invention, the incidence of cucumber *Pseudoperonospora cubensis* was greatly reduced compared to the non-treated region, and significantly high control effects were obtained.

TABLE 4

|  | Diseased area rate | Control titer (%) |
| --- | --- | --- |
| Treated region (Formulation Example 1) | 4 | 88.6 |
| Treated region (Formulation Example 3) | 3 | 91.4 |
| Comparative region (Impression wettable powder) | 25 | 28.6 |
| Non-treatment region | 35 | 0.0 |

Example 5 and Comparative Example 5

Test for the Effects on Apple *Altenaria Alternaria mali*

Leaves of apples (variety: Orin) were collected and sufficient doses of the wettable powders in Formulation Examples 1 and 3 with the dilution rate of 250 times were sprayed by a spray gun on the back side of the leaves. As a comparative example, the diluent of Impression wettable powder (produced by SDS Biotech K.K.) with the dilution rate of 250 times was also subjected to the test in the same manner. After spraying, the leaves were air-dried and the suspension of the apple *Altenaria Alternaria mali* spores was sprayed and inoculated thereto. After the leaves were left to stand at 20° C. in humid condition for four days, the diseased area rate was investigated with eyes to thereby determine the control titer. The control titer (%) was calculated on the basis of the diseased area rate in the non-treatment region. As can be seen from the results in Table 5, by the treatment with the microbiological agent of the present invention, the incidence of apple *Altenaria Alternaria mali* was greatly reduced compared to the non-treated region, and significantly high control effects were obtained.

TABLE 5

|  | Diseased area rate | Control titer (%) |
| --- | --- | --- |
| Treated region (Formulation Example 1) | 5 | 91.7 |
| Treated region (Formulation Example 3) | 7 | 88.3 |
| Comparative region (Impression wettable powder) | 30 | 50.0 |
| Non-treatment region | 60 | 0.0 |

Example 6 and Comparative Example 6

Test for the Effects on Cucumber *Sphaerotherca Fuliginea* (Field Test)

The test was performed in the company-owned greenhouse using cucumbers (test region: 4 m²/region; 10 plants/region; in triplicate). The disease was allowed to occur naturally. The wettable powders in Formulation Examples 1 and 3 with the dilution rate of 500 times, 1,000 times and 2,000 times were sprayed four times at intervals of seven days and the control titer (%) was calculated from the disease area rate on the leaves. The Impression wettable powder (SDS Biotech K.K.) with the dilution rate of 500 times and 1,000 times, Botokiller wettable powder (Idemitsu Kosan Co., Ltd.) with the dilution rate of 1,000 times, Botopika wettable powder (Idemitsu Kosan Co., Ltd.) with the dilution rate of 2,000 times, Ecoshot granule wettable powder (Kumiai Chemical Industry Co., Ltd.) with the dilution rate of 1,000 times and Morestan wettable powder (Agro-Kanesho Co., Ltd.) with the dilution rate of 3,000 times were used as a comparative agent. The incidence of the disease in the non-treated region was 47.4%. The control titer (%) was calculated on the basis of the incidence in the non-treatment region. As can be seen from the results in Table 6, by the treatment with the microbiological agent of the present invention, the incidence of cucumber *Sphaerotherca fuliginea* was greatly reduced compared to the non-treated region, and significantly high control effects were obtained. A remarkably higher effect was confirmed in the field as well compared to conventional commercially-available *Bacillus subtilis* agents (Impression wettable powder (Patent Document 3), Botokiller wettable powder, Botopica wettable powder, Ecoshot wettable powder (Patent Document 4)) used as a comparative agent. The microbiological agent of the present invention with the dilution rate of 500 times showed a very high effect equivalent to the Morestan wettable powder, which is a chemical agent.

TABLE 6

|   | Incidence | Control titer |
|---|---|---|
| Treated region (Formulation Example 1), dilution rate: 500 times | 2.1 | 95.6 |
| Treated region (Formulation Example 1), dilution rate: 1,000 times | 6.2 | 86.9 |
| Treated region (Formulation Example 1), diluent rate: 2,000 times | 10.3 | 78.3 |
| Treated region (Formulation Example 3), dilution rate: 500 times | 4.2 | 91.1 |
| Treated region (Formulation Example 3), dilution rate: 1,000 times | 5.7 | 88.0 |
| Treated region (Formulation Example 3), dilution rate: 2,000 times | 10 | 78.9 |
| Comparative Region (Impression wettable powder), dilution rate: 500 times | 17.9 | 62.2 |
| Comparative Region (Botokiller wettable powder), dilution rate: 1,000 times | 35.3 | 25.5 |
| Comparative Region (Botopika wettable powder), dilution rate: 2,000 times | 34.4 | 27.4 |
| Comparative region (Ecoshot granular wettable powder), diluent rate: 1,000 times | 37.5 | 20.9 |
| Comparative region (Morestan wettable powder) diluent rate: 3,000 times | 1.1 | 97.7 |
| Non-treatment region | 47.4 | 0.0 |

Example 7 and Comparative Example 7

Test for the Effects on Eggplant *Botrytis cinerea* (Field Test)

The test was performed in the company-owned greenhouse using eggplants (test region: 5.6 m²/region; 7 plants/region; in triplicate). The disease was allowed to occur naturally. The wettable powders in Formulation Examples 1 and 3 with the dilution rate of 500 times and 1,000 times were sprayed four times at intervals of seven days and the control titer (%) was calculated from the incidence in the fruits. The Impression wettable powder (SDS Biotech K.K.) with the dilution rate of 500 times and 1,000 times, Botokiller wettable powder (Idemitsu Kosan Co., Ltd.) with the dilution rate of 1,000 times, Botopika wettable powder (Idemitsu Kosan Co., Ltd.) with the dilution rate of 2,000 times, Ecoshot granule wettable powder (Kumiai Chemical Industry Co., Ltd.) with the dilution rate of 1,000 times and Savior Flowable 20 (Syngenta Japan K.K.) with the dilution rate of 1,500 times were used as a comparative agent. The incidence of the disease in the non-treated region was 15%. The control titer (%) was calculated on the basis of the incidence in the non-treatment region. As can be seen from the results in Table 7, by the treatment with the microbiological agent of the present invention, the incidence of *Botrytis cinerea* was greatly reduced compared to the non-treated region, and significantly high control effects were obtained. A remarkably higher effect was confirmed in the field as well compared to conventional commercially-available *Bacillus subtilis* agents (Impression wettable powder, Botokiller wettable powder, Botopica wettable powder, Ecoshot wettable powder) used as a comparative agent. The microbiological agent of the present invention with the dilution rate of 500 times showed a very high effect equivalent to Savior Flowable 20, which is a chemical agent.

TABLE 7

|   | Incidence | Control titer |
|---|---|---|
| Treated region (Formulation Example 1), dilution rate: 500 times | 2.4 | 84.0 |
| Treated region (Formulation Example 1), dilution rate: 1,000 times | 4.1 | 72.7 |
| Treated region (Formulation Example 3), dilution rate: 500 times | 2.9 | 80.7 |
| Treated region (Formulation Example 3), dilution rate: 1,000 times | 4.1 | 72.7 |
| Comparative Region (Impression wettable powder), dilution rate: 500 times | 6.8 | 54.7 |
| Comparative Region (Botokiller wettable powder), dilution rate: 1,000 times | 8.8 | 41.3 |
| Comparative Region (Botopika wettable powder), dilution rate: 2,000 times | 6.9 | 54.0 |
| Comparative region (Ecoshot granular wettable powder), diluent rate: 1,000 times | 7.2 | 52.0 |
| Comparative region (Savior Flowable 20), diluent rate: 1,500 times | 2.1 | 86.0 |
| Non-treatment region | 15 | 0.0 |

Example 8 and Comparative Example 8

Test for the Effects on *Burkholderia plantarii*

The seed rice (variety: Koshihikari) was immersed to be inoculated in the suspension of *Burkholderia plantarii* ($1 \times 10^8$ CFU/ml), which was obtained by the shake culture on the PD liquid medium at 27° C. for 52 hours, for one hour under reduced pressure to thereby prepare the seeds infected with *Burkholderia plantarii*. The seeds infected with *Burkholderia plantarii* were immersed in the solution of the wettable powder of Formulation Example 1 and Formulation Example 3 with the dilution rate of 100 times. After the solution was removed, the seeds were retained in a humidity room of 32° C. for one day to stimulate the germination. As a comparative agent, the solution of Impression (SDS Biotech K.K.) with the dilution rate of 100 times was also subjected to the test in the same manner. The germination-stimulated seeds were seeded in a plastic cup having a diameter of 6 cm filled with culture soil. The seedlings were retained in a room for raising seedlings at 30° C. for three days after the seeding and in a humidity room at 25° C. for 15 days. Then all of the seedlings were investigated for the presence of the disease to determine the diseased seedling rate. The control titer (%) was calculated on the basis of the diseased seedling rate in the non-treated region. The seeding amount per cup was 3 g of dry seed rice (90 to 110 grains). As can be seen from the results in Table 8, by the treatment with the microbiological agent of the present invention, the rate of diseased seedlings of *Burkholderia plantarii* was greatly reduced compared to the non-treated region, and significantly high control effects were obtained.

TABLE 8

|   | Diseased seedling rate | Control titer (%) |
|---|---|---|
| Treated region (Formulation Example 1) | 30 | 60.0 |
| Treated region (Formulation Example 3) | 35 | 53.3 |
| Comparative region (Impression wettable powder) | 55 | 26.7 |
| Non-treatment region | 75 | 0.0 |

Example 9 and Comparative Example 9

Test for the Effect on *Rhizoctonia solani*

3 g of the culture product of *Rhizoctonia solani* in a bran medium was mixed into 500 ml of sterilized soil to be filled in a plastic pot, and 1 g of the granular formulation of Formulation Example 2 and Formulation Example 4 was mixed into the soil, respectively. As a comparative agent, 84 mg of Impression wettable powder was also subjected to the test in the same manner. Cucumbers (variety: Sagami-hanjiro) were seeded and after growing the cucumbers at 23° C. for one week, the germination rate was investigated. The control effect (control titer %) was calculated on the basis of the diseased seedling rate in the non-treated region. As can be seen from the results in Table 9, by the treatment with the microbiological agent of the present invention, the rate of the diseased seedlings of *Rhizoctonia solani* was greatly reduced compared to the non-treated region, and significantly high control effects were obtained.

TABLE 9

|  | Diseased seedling rate | Control titer (%) |
| --- | --- | --- |
| Treated region (Formulation Example 2) | 12 | 60.0 |
| Treated region (Formulation Example 4) | 18 | 40.0 |
| Comparative region (Impression wettable powder) | 23 | 23.3 |
| Non-treatment region | 30 | 0.0 |

Example 10 and Comparative Example 10

Activity Against the Second-Stage Larva of Sweetpotato *Meloidogyne* sp

The nematicidal activity against the second-stage larva of sweetpotato *Meloidogyne* sp. hatched within 24 hours from the egg capsule collected from the roots of eggplants (variety: Juryo). Each of the solutions of Formulation 1 and Formulation 3 with the dilution rate of 100 times (a Tween 20 solution with the dilution rate of 5,000 times) and an equivalent amount of the second-stage larva of sweetpotato *Meloidogyne* sp. (about 50 worms) were added to a 24-hole microplate. As a comparative agent, the Impression (SDS Bioteck K.K.) solution with the dilution rate of 100 times was also subjected to the test in the same manner. The plate was sealed and placed in an incubator at 28° C. and relative humidity of about 50%. After 72 hours, the death rate was investigated by an observation by a stereoscopic microscope. At that time, immobile nematodes were regarded as being dead. The nematicidal rate was calculated according to the expression described below. As can be seen from the results in Table 10, by the treatment with the microbiological agent of the present invention, an extremely high nematicidal activity was obtained against the second-stage larva of sweetpotato *Meloidogyne* sp.

Nematicidal rate=(number of dead nematodes/number of tested nematodes)×100 [Expression 1]

TABLE 10

|  | Nematicidal rate |
| --- | --- |
| Treated region (Formulation Example 1) | 100 |
| Treated region (Formulation Example 3) | 100 |
| Comparative region (Impression wettable powder) | 10 |
| Non-treatment region | 5 |

Example 11 and Comparative Example 11

Test for the Control Effect Against Sweetpotato *Meloidogyne* sp.

In a 1/10,000 a-Wagner pot, each of the granular formulation of Formulation Example 2 and Formulation Example 4 was uniformly mixed in the soil infected with sweetpotato *Meloidogyne* sp. at the rate of 40 kg/10 a and small-size tomatoes (variety: Sugar lump) were planted thereto. As a comparative agent, Impression wettable powder (SDS Biotech K.K.) was also subjected to the test in the same manner at the rate of 3.3 kg/10 a. One month after the settled planting, the degree of damage to the roots (root-knot degree) was classified and evaluated according to the criteria described below. The root-knot index was determined according to the expression as below to calculate the control titer. As can be seen from the results in Table 11, by the treatment with the microbiological agent of the present invention, the root damages caused by sweetpotato *Meloidogyne* sp. were greatly reduced compared to the non-treated region, and significantly high control effects were obtained.

Degree of damage 0: No root-knot was observed.

1: The root-knots are hardly-noticeable at a glance but a few can be found.

2: A few of root-knots are observed.

3: Moderate amount of root-knots are observed.

4: A number of root-knows are observed all over the rhizosphere.

Root-knot index=(Σ(degree of damage×number of units)/all of the investigated population×4)×100

Control titer=(1−Root-knot index in the treated region/Root-knot index in the non-treated region)×100 [Expression 2]

TABLE 11

|  | Degree of damage | Root-knot index | Control titer |
| --- | --- | --- | --- |
| Treated region (Formulation Example 2) | 1.2 | 30 | 70.0 |
| Treated region (Formulation Example 4) | 2 | 50 | 50.0 |
| Comparative region (Impression wettable powder) | 3.5 | 87.5 | 12.5 |
| Non-treatment region | 4 | 100 | 0.0 |

Example 12 and Comparative Examples 12 to 13

Effect of Promoting Plant Growth of the AT-332 Strain (Basic Test)

A petri plate basic test was carried out with respect to *Arabidopsis thaliana* to measure the effect of promoting plant growth of the AT-332 strain. After immersing the seeds of *Arabidopsis thaliana* in 1% sodium hypochlorite for 20 minutes, the seeds are immersed in 70% ethanol solution for two minutes to sterilize the surface of the seeds. After that, the seeds were washed with sterile distilled water to be used for the test. A Murashige and Skoog salt medium (pH 5.7) containing 0.8% agar was poured into a dual-partitioning sterile petri plate and used for a test after being cooled.

Figure 2:
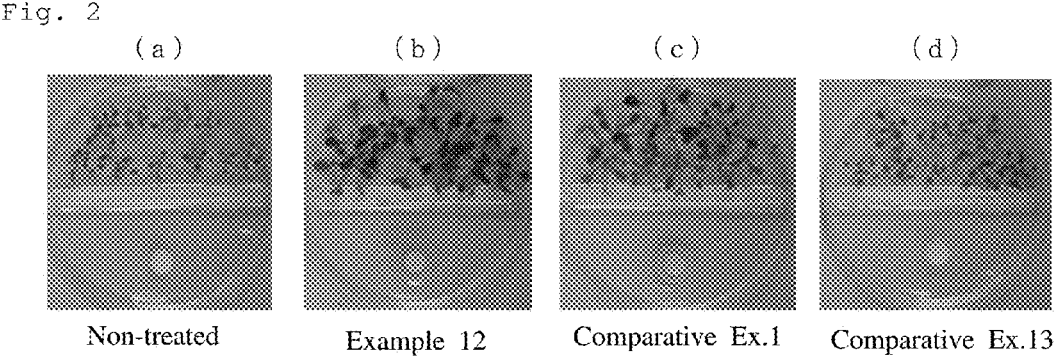
FIG. 2 Photographs (a) to (d) show the effect of promoting plant growth of the AT-332 strain in the basic test (Example 12 and Comparative Examples 12-13).

The AT-332 (Example 12), *Bacillus subtilis* GB03 (Comparative Example 12) and *Bacillus subtilis* MBI600 (Comparative Example 13) were inoculated respectively on a sterile paper disc placed on one of the divided portion of the above petri plate, and germinated seeds of *Arabidopsis thaliana* were inoculated in the other portion of the petri plate. The plate inoculated with the bacteria and *Arabidopsis thaliana* was retained at 22° C. (12 hours in light/12 hours being cut off from the light) for ten days and the plant growth status was observed. The results are shown in photographs (a) to (d) in FIG. 2 including the results of the control (FIG. 2 (*a*)) where the bacteria were not inoculated. A remarkable effect of promoting plant growth was confirmed with the AT-332 (Example 12; (b)) compared to *Bacillus subtilis* GB03 (Comparative Example 12; photo (c)) and *Bacillus subtilis* MBI600 (Comparative Example 13; photo (d)), which are actually sold and used in the United State market.

Example 13

Effect of Promoting Plant Growth of the AT-332 and AT-79 Strains (Pot Test)

Figure 3:
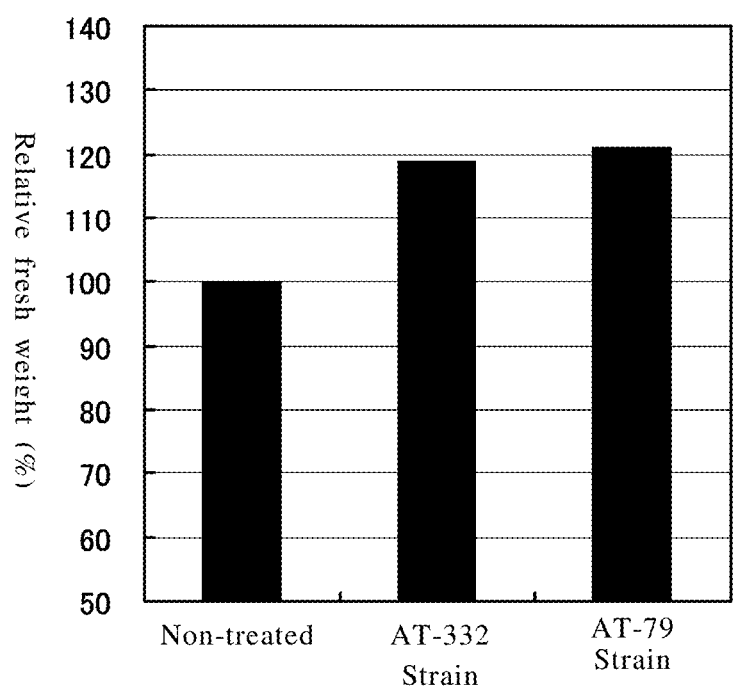
FIG. 3 shows the effect of promoting growth of Chinese cabbage of the AT-332 and AT-79 strains in a pot test (Example 13).

A pot test was carried out with respect to Chinese cabbage seedlings to measure the plant growth promoting effect of the AT-332 and AT-79 strains. After culturing the AT-332 and AT-79 strains in a liquid LB medium for 24 hours, the bacteria cells were collected by centrifugation. The collected bacteria cells were suspended in a 0.85% sodium chloride aqueous solution so as to be contained at a concentration of $1 \times 10^9$ CFU/ml. 40 ml of the suspension was mixed per 1 kg of the previously sterilized culture soil to serve as the treated soil. On the other hand, 40 ml of 0.85% sodium chloride aqueous solution was mixed per 1 kg of the previously sterilized culture soil to serve as the non-treated soil. 100 g of each of the treated soil and non-treated soil was put in a plastic pot (70 mm in diameter×68 mm in height) respectively, and seeds of Chinese cabbage (variety: Nozaki Chinese Cabbage No. 2) were sowed in the pot. Subsequently, the pots were placed in greenhouse set at 22° C. and the fresh weight of the grown Chinese cabbage was measured after 30 days. The results are shown in FIG. 3. An explicit effect of promoting the crop growth of the AT-332 and AT-79 strains was confirmed.

The invention claimed is:

1. A bacteria selected from the group consisting of: (a) *Bacillus* sp. AT-332 strain (deposited under Accession No. NITE BP-1095), containing the 16S rDNA sequence of SEQ ID NO: 2; and (b) *Bacillus* sp. AT-79 strain (deposited under Accession No. NITE BP-1094), containing the 16S rDNA sequence of SEQ ID NO: 3, wherein said bacteria is stabilized in a dried form.

2. The bacteria of claim 1, wherein said bacteria exhibits an effect of controlling plant diseases, controlling nematodes, and/or promoting plant growth.

3. The bacteria of claim 1, wherein the bacteria is *Bacillus* sp. AT-79 strain (deposited under Accession No. NITE BP-1094), containing the 16S rDNA sequence of SEQ ID NO: 3.

4. A microbiological agent containing at least one of the bacteria of claim 1.

5. The microbiological agent of claim 4, which is a plant disease control agent.

6. The microbiological agent of claim 4, which is a nematode control agent.

7. The microbiological agent of claim 4, which is a plant growth promoter.

8. The bacteria of claim 1, wherein the bacteria is *Bacillus* sp. AT-332 strain (deposited under Accession No. NITE BP-1095), containing the 16S rDNA sequence of SEQ ID NO: 2.

* * * * *

SEQUENCE LISTING

```
<160> NUMBER OF SEQ ID NOS: 3

<210> SEQ ID NO 1
<211> LENGTH: 1472
<212> TYPE: DNA
<213> ORGANISM: Bacillus sp. AT-332 / AT-79

<400> SEQUENCE: 1
gacgaacgct ggcggcgtgc ctaatacatg caagtcgagc ggacagatgg gagcttgctc      60
cctgatgtta gcggcggacg ggtgagtaac acgtgggtaa cctgcctgta agactgggat     120
aactccggga aaccggggct aataccggat gcttgtttga accgcatggt tcagacataa     180
aaggtggctt cggctaccac ttacagatgg acccgcggcg cattagctag ttggtgaggt     240
aacggctcac caaggcgacg atgcgtagcc gacctgagag ggtgatcggc cacactggga     300
ctgagacacg gcccagactc ctacgggagg cagcagtagg gaatcttccg caatggacga     360
aagtctgacg gagcaacgcc gcgtgagtga tgaaggtttt cggatcgtaa agctctgttg     420
ttagggaaga acaagtgccg ttcraatagg gcggcacctt gacggtacct aaccagaaag     480
ccacggctaa ctacgtgcca gcagccgcgg taatacgtag gtggcaagcg ttgtccggaa     540
ttattgggcg taaagggctc gcaggcggtt tcttaagtct gatgtgaaag cccccggctc     600
aaccggggag ggtcattgga aactgggaa cttgagtgca gaagaggaga gtggaattcc      660
acgtgtagcg gtgaaatgcg tagagatgtg gaggaacacc agtggcgaag gcgactctct     720
ggtctgtaac tgacgctgag gagcgaaagc gtggggagcg aacaggatta gataccctgg     780
tagtccacgc cgtaaacgat gagtgctaag tgttaggggg tttccgcccc ttagtgctgc     840
agctaacgca ttaagcactc cgcctgggga gtacggtcgc aagactgaaa ctcaaaggaa     900
ttgacggggg cccgcacaag cggtggagca tgtggtttaa ttcgaagcaa cgcgaagaac     960
cttaccaggt cttgacatcc tctgacaatc ctagagatag gacgtcccct tcgggggcag    1020
agtgacaggt ggtgcatggt tgtcgtcagc tcgtgtcgtg agatgttggg ttaagtcccg    1080
caacgagcgc aacccttgat cttagttgcc agcattcagt tgggcactct aaggtgactg    1140
```

```
ccggtgacaa accggaggaa ggtggggatg acgtcaaatc atcatgcccc ttatgacctg      1200
ggctacacac gtgctacaat gggcagaaca aagggcagcg araccgcgag gttaagccaa      1260
tcccacaaat ctgttctcag ttcggatcgc agtctgcaac tcgactgcgt gaagctggaa      1320
tcgctagtaa tcgcggatca gcatgccgcg gtgaatacgt tcccgggcct tgtacacacc      1380
gcccgtcaca ccacgagagt ttgtaacacc cgaagtcggt gaggtaacct ttttggagcc      1440
agccgccgaa ggtgggacag atgattgggg tg                                    1472
```

<210> SEQ ID NO 2
<211> LENGTH: 1472
<212> TYPE: DNA
<213> ORGANISM: Bacillus sp. AT-332

<400> SEQUENCE: 2

```
gacgaacgct ggcggcgtgc ctaatacatg caagtcgagc ggacagatgg gagcttgctc        60
cctgatgtta gcggcggacg ggtgagtaac acgtgggtaa cctgcctgta agactgggat       120
aactccggga aaccggggct aataccggat gcttgtttga accgcatggt tcagacataa       180
aaggtggctt cggctaccac ttacagatgg acccgcggcg cattagctag ttggtgaggt       240
aacggctcac caaggcgacg atgcgtagcc gacctgagag ggtgatcggc cacactggga       300
ctgagacacg gcccagactc ctacgggagg cagcagtagg gaatcttccg caatggacga       360
aagtctgacg gagcaacgcc gcgtgagtga tgaaggtttt cggatcgtaa agctctgttg       420
ttagggaaga acaagtgccg ttcgaatagg gcggcacctt gacggtacct aaccagaaag       480
ccacggctaa ctacgtgcca gcagccgcgg taatacgtag gtggcaagcg ttgtccggaa       540
ttattgggcg taaagggctc gcaggcggtt tcttaagtct gatgtgaaag ccccggctc       600 aaccggggag ggtcattgga aactgggaa cttgagtgca agagaggaga gtggaattcc       660
acgtgtagcg gtgaaatgcg tagagatgtg gaggaacacc agtggcgaag gcgactctct       720
ggtctgtaac tgacgctgag gagcgaaagc gtggggagcg aacaggatta gataccctgg       780
tagtccacgc cgtaaacgat gagtgctaag tgttaggggg tttccgcccc ttagtgctgc       840
agctaacgca ttaagcactc cgcctgggga gtacggtcgc aagactgaaa ctcaaaggaa       900
ttgacggggg cccgcacaag cggtggagca tgtggtttaa ttcgaagcaa cgcgaagaac       960
cttaccaggt cttgacatcc tctgacaatc ctagagatag gacgtcccct tcggggcag      1020 agtgacaggt ggtgcatggt tgtcgtcagc tcgtgtcgtg agatgttggg ttaagtcccg      1080
caacgagcgc aacccttgat cttagttgcc agcattcagt tgggcactct aaggtgactg      1140
ccggtgacaa accggaggaa ggtggggatg acgtcaaatc atcatgcccc ttatgacctg      1200
ggctacacac gtgctacaat gggcagaaca aagggcagcg aaaccgcgag gttaagccaa      1260
tcccacaaat ctgttctcag ttcggatcgc agtctgcaac tcgactgcgt gaagctggaa      1320
tcgctagtaa tcgcggatca gcatgccgcg gtgaatacgt tcccgggcct tgtacacacc      1380
gcccgtcaca ccacgagagt ttgtaacacc cgaagtcggt gaggtaacct ttttggagcc      1440
agccgccgaa ggtgggacag atgattgggg tg                                    1472
```

<210> SEQ ID NO 3
<211> LENGTH: 1472
<212> TYPE: DNA
<213> ORGANISM: Bacillus sp. AT-79

<400> SEQUENCE: 3

```
gacgaacgct ggcggcgtgc ctaatacatg caagtcgagc ggacagatgg gagcttgctc         60
cctgatgtta gcggcggacg ggtgagtaac acgtgggtaa cctgcctgta agactgggat        120
aactccggga aaccggggct aataccggat gcttgtttga accgcatggt tcagacataa        180
aaggtggctt cggctaccac ttacagatgg acccgcggcg cattagctag ttggtgaggt        240
aacggctcac caaggcgacg atgcgtagcc gacctgagag ggtgatcggc cacactggga        300
ctgagacacg gcccagactc ctacgggagg cagcagtagg gaatcttccg caatggacga        360
aagtctgacg gagcaacgcc gcgtgagtga tgaaggtttt cggatcgtaa agctctgttg        420
ttagggaaga acaagtgccg ttcaaatagg gcggcacctt gacggtacct aaccagaaag        480
ccacggctaa ctacgtgcca gcagccgcgg taatacgtag gtggcaagcg ttgtccggaa        540
ttattgggcg taaagggctc gcaggcggtt tcttaagtct gatgtgaaag cccccggctc        600
aaccggggag ggtcattgga aactgggaa cttgagtgca gaagaggaga gtggaattcc         660
acgtgtagcg gtgaaatgcg tagagatgtg gaggaacacc agtggcgaag gcgactctct        720
ggtctgtaac tgacgctgag gagcgaaagc gtggggagca aacaggatta gatacctgg        780 tagtccacgc cgtaaacgat gagtgctaag tgttaggggg tttccgcccc ttagtgctgc        840
agctaacgca ttaagcactc cgcctgggga gtacggtcgc aagactgaaa ctcaaaggaa        900
ttgacggggg cccgcacaag cggtggagca tgtggtttaa ttcgaagcaa cgcgaagaac        960
cttaccaggt cttgacatcc tctgacaatc ctagagatag gacgtccct tcgggggcag       1020 agtgacaggt ggtgcatggt tgtcgtcagc tcgtgtcgtg agatgttggg ttaagtcccg       1080
caacgagcgc aacccttgat cttagttgcc agcattcagt tgggcactct aaggtgactg       1140
ccggtgacaa accggaggaa ggtggggatg acgtcaaatc atcatgcccc ttatgacctg       1200
ggctacacac gtgctacaat gggcagaaca aagggcagcg agaccgcgag gttaagccaa       1260
tcccacaaat ctgttctcag ttcggatcgc agtctgcaac tcgactgcgt gaagctggaa       1320
tcgctagtaa tcgcggatca gcatgccgcg gtgaatacgt tcccgggcct tgtacacacc       1380
gcccgtcaca ccacgagagt ttgtaacacc cgaagtcggt gaggtaacct ttttggagcc       1440
agccgccgaa ggtgggacag atgattgggg tg                                     1472
```